(12) United States Patent
Larrow et al.

(10) Patent No.: US 6,781,006 B2
(45) Date of Patent: Aug. 24, 2004

(54) ACTIVE CATALYSTS FOR STEREOSELECTIVE RING-OPENING REACTIONS

(75) Inventors: Jay F. Larrow, Wakefield, MA (US); Karl Hemberger, Essex, MA (US); Hocine Kabir, Serezin du Rhone (FR); Philippe Morel, Chuzelles (FR)

(73) Assignee: Rhodia Pharma Solutions Inc., Cranbury, NJ (US)

( * ) Notice: Subject to any disclaimer, the term of this patent is extended or adjusted under 35 U.S.C. 154(b) by 0 days.

(21) Appl. No.: 10/245,110

(22) Filed: Sep. 17, 2002

(65) Prior Publication Data

US 2004/0053779 A1 Mar. 18, 2004

(51) Int. Cl.$^7$ .......................... C07F 11/00; C07F 15/06; B01J 31/00
(52) U.S. Cl. .......................... 556/32; 556/34; 549/230; 502/158; 502/167
(58) Field of Search ...................... 556/32, 34; 502/158, 502/167; 549/230

(56) References Cited

U.S. PATENT DOCUMENTS

| | | | | |
|---|---|---|---|---|
| 4,746,748 | A | * 5/1988 | Aoki et al. | ..... 556/34 |
| 5,637,739 | A | 6/1997 | Jacobsen et al. | ..... 549/524 |
| 5,663,393 | A | 9/1997 | Jacobsen et al. | ..... 556/45 |
| 5,665,890 | A | 9/1997 | Jacobsen et al. | ..... 549/230 |
| 5,929,232 | A | 7/1999 | Jacobsen et al. | ..... 540/145 |
| 6,262,278 | B1 | 7/2001 | Jacobsen et al. | ..... 549/230 |

OTHER PUBLICATIONS

Tokunaga, M.; Larrow, J.F.; Kakiuchi, F.; Jacobsen, E.N. "Asymmetric Catalysis with Water: Efficient Kinetic Resolution of Terminal Epoxides by Means of Catalytic Hydrolysis," Science 1997 277, 936–938.

Furrow, M.E., Schaus, S.E., Jacobsen, E.N. "Practical Access to Highly Enantioenriched C–3 Building Blocks via Hydrolytic Kinetic Resolution," J. Org. Chem. 1998, 63, 6776.

Schaus, S.E.; Brandes, B.D.; Larrow, J.F.; Tokunaga, M.; Hansen, K.B.; Gould A.E., Furrow, M.E.; Jacobsen, E.N. "Highly Selective Hydrolytic Kinetic Resolution of Terminal Epoxides Catalyzed by Chiral (salen)Cobalt III) Complexes. Practical Synthesis of Enantioenriched Terminal Epoxides and 1,2–Diols," J. Am. Chem. Soc 2002, 124, 1307.

* cited by examiner

Primary Examiner—Porfirio Nazario-Gonzalez

(57) ABSTRACT

A method for making a chiral transition metal-ligand catalyst complex that is active in catalyzing stereoselective ring opening reactions includes contacting an asymmetric tetradentate ligand, in an excess of a Brønsted acid, with a salt of a first row transition metal, wherein the acidity of the conjugate acid of the salt is the same as or less than the acidity of the Brønsted acid, under conditions effective to allow formation of the active chiral transition metal-ligand catalyst complex, and forming a solution of the complex in a water-miscible, protic solvent from which the active complex can be precipitated by the addition of water and adding water to the solution to precipitate at least a portion of the complex.

30 Claims, No Drawings

_US 6,781,006 B2_

ACTIVE CATALYSTS FOR STEREOSELECTIVE RING-OPENING REACTIONS

FIELD OF THE INVENTION

The present invention is directed to catalysts, more particularly, active transition metal-ligand catalyst complexes, for use in catalyzing stereoselective ring opening reactions.

BACKGROUND OF THE INVENTION

The stereoselective reaction of various nucleophiles in the ring-opening of epoxides catalyzed by chiral (salen)Co(III) complexes provides ready access to a large number of enantiomerically enriched chiral products useful to the pharmaceutical, agrochemical and flavor and fragrance industries. These products can be accessed via the kinetic resolution of racemic epoxides using sub-stoichiometric amounts of the nucleophile or via the stereoselective stoichiometric reaction of a nucleophile with a resolved epoxide. For these processes, the generation of the active Co(III) catalyst, either from inactive Co(II) species or from the chiral ligand and a metal salt, requires the use of a suitable solvent (typically a chlorinated hydrocarbon such as methylene chloride), a Brønsted acid (typically acetic acid), and air or oxygen. In the published procedures, the generation of active catalyst is typically performed each time the ring-opening reaction is run, and is subject to variability in quality and performance. U.S. Pat. Nos. 5,665,890, 5,929, 232, 5,663,393, 5,637,739, 6,262,278, Tokunaga, M.; Larrow, J. F.; Kakiuchi, F.; Jacobsen, E. N. "Asymmetric Catalysis with Water: Efficient Kinetic Resolution of Terminal Epoxides by Means of Catalytic Hydrolysis," _Science_ 1997 277, 936–938. Schaus, S. E.; Brandes, B. D.; Larrow, J. F.; Tokunaga, M.; Hansen, K. B.; Gould, A. E.; Furrow, M. E.; Jacobsen, E. N. "Highly Selective Hydrolytic Kinetic Resolution of Terminal Epoxides Catalyzed by Chiral (salen)Cobalt(III)-Complexes. Practical Synthesis of Enantioenriched Terminal Epoxides and 1,2-Diols," _J. Am. Chem. Soc_ 2002, 124, 1307. Furrow, M. E., Schaus, S. E., Jacobsen, E. N. "Practical Access to Highly Enantioenriched C-3 Building Blocks via Hydrolytic Kinetic Resolution" _J. Org. Chem._ 1998, 63, 6776.

Currently, catalyst activation involves the reacting of inactive (salen)Co(II) complex with 2 equivalents of acetic acid in methylene chloride. Air is sparged through the mixture for several hours (depending on scale) to form the active (salen)Co(III)OAc catalyst and water (from the reduction of $O_2$). At this point, the solvent is removed by reduced pressure distillation, which deposits the catalyst as a film of an amorphous solid on the walls of the vessel. There are several issues with this process which become magnified on scale. First, the sparging of air requires the use of a nonflammable solvent, or one with a high flashpoint due to the generation of air-solvent vapor mixtures. Since methylene chloride is low boiling and an environmental hazard, its vapor must be removed from the air effluent prior to release to the atmosphere. This requires scrubbing equipment that must be maintained. Second, the solvent removal takes time, which makes the process more costly, and the complete removal of solvent is virtually impossible, especially on larger scale. The residual solvent must then be removed from the product after the ring-opening reaction, which introduces further costs. Next, because the activation reaction is performed each time, there is an undesirable element of variability every time the ring-opening reaction is performed.

SUMMARY OF THE INVENTION

In a first aspect, the present invention is directed to a method for making a chiral catalyst complex, comprising:

contacting an asymmetric tetradentate ligand with a Brønsted acid, a Co(II) or Cr(II) salt, wherein the acidity of the conjugate acid of the salt is the same as or less than the acidity of the Brønsted acid, and an oxidant under conditions effective to allow formation of a chiral catalyst complex of Co(III) or Cr(III) and the ligand, forming a solution of the complex in a water-miscible, protic solvent from which the complex can be precipitated by the addition of water, and adding water to the solution to precipitate at least a portion of the complex.

In a second aspect, the present invention is directed to a method for making a chiral catalyst complex in particulate solid form, comprising:

providing a solution of a chiral catalyst complex of Co(III) or Cr(III) with an asymmetric tetradentate ligand in a water-miscible, protic solvent comprising a compound selected from methanol, ethanol, n-propanol and 1-methoxy-2-propanol, adding water to the solution to precipitate at least a portion of the complex, and isolating the precipitated complex as a particulate solid.

In a third aspect, the present invention is directed to a catalyst active in catalyzing stereoselective ring opening reactions, comprising a chiral catalyst complex of Co(III) or Cr(III) with an asymmetric tetradentate ligand and a counterion or nucleophile selected from carboxylate, hydroxide, alkoxide thiolate, sulfonate, sulfonamide, isocyanate, isothiocyanate, and halide, wherein the complex is in crystalline solid form.

In a fourth aspect, the present invention is directed to a method for stereoselective ring opening, comprising:

providing, in crystalline solid form, a chiral catalyst complex of Co(III) or Cr(III) with an asymmetric tetradentate ligand and a counterion or nucleophile selected from carboxylate, hydroxide, alkoxide, thiolate, sulfonate, sulfonamide, isocyanate, isothiocyanate, or halide that is active in catalyzing nucleophilic attack by a nucleophile of a chiral or prochiral cyclic substrate, wherein said substrate comprises a carbocycle or a heterocycle having a reactive center susceptible to the nucleophilic attack by the nucleophile, reacting the nucleophile and the chiral or prochiral cyclic substrate in the presence of a catalytic amount of the catalyst complex under conditions effective to allow production of a stereoisomerically enriched product.

In a fifth aspect, the present invention is directed to a method for providing a chiral catalyst complex having known activity in catalyzing a stereoselective ring opening reaction, comprising:

isolating a chiral catalyst complex of Co(III) or Cr(III) with an asymmetric tetradentate ligand, using a portion of the isolated complex to catalyze a first stereoselective ring opening reaction, and characterizing the reaction rate of the first reaction, and providing the remaining isolated complex for use in catalyzing stereoselective ring opening reactions analogous to the first stereoselective ring opening reaction

DESCRIPTION OF INVENTION AND PREFERRED EMBODIMENTS

For convenience, certain terms used in this application are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions.

The terms "electrophilic atom", "electrophilic center" and "reactive center" as used herein refer to the atom of the substrate which is attacked by, and forms a new bond to, the nucleophile. In most (but not all) cases, this will also be the atom from which a leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of asymmetry and whose molecules are not mirror images of one another.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "reaction product" means a compound which results from the reaction of a nucleophile and a substrate. In general, the term "reaction product" will be used herein to refer to a stable, isolable compound, and not to unstable intermediates or transition states.

As used herein in reference to a ligand or catalyst complex, the term "asymmetric" means that the ligand or complex comprises chiral centers that are not related by a plane or point of symmetry and/or that the ligand or complex comprises an axis of asymmetry due to, for example, restricted rotation, helicity, molecular knotting or chiral metal complexation.

As used herein in reference to a ligand, the term "tetradentate" means that the ligand comprises four Lewis base substituents, which may be selected from, for example, oxygen atoms, sulfur atoms, nitrogen containing substituents, such as amino, amido, or imino groups, phosphorus-containing substituents, such as phosphine or phosphonate groups, and arsenic-containing substituents, such as arsine groups.

As used herein in reference to a complex of a metal atom and a tetradentate ligand, the term "rectangular planar" refers to a geometric configuration in which, subject to some distortion, the Lewis basic atoms of the complex each lie in substantially the same plane and are in a substantially rectangular arrangement and the metal atom of the complex lies in substantially the same plane.

As used herein to a complex of a metal atom and a tetradentate ligand, the term "rectangular pyramidal" refers to a geometric configuration in which, subject to some distortion, the Lewis basic atoms of the complex each lie in substantially the same plane and are in a substantially rectangular arrangement and the metal atom of the complex lies above or below the plane.

The term "complex" as used herein means a coordination compound formed by the union of one or more electronically rich molecules or atoms capable of independent existence with one or more electronically poor molecules or atoms, each of which is also capable of independent existence.

The term "substrate" is intended to mean a chemical compound which can react with a nucleophile, or with a ring-expansion regent, according to the present invention, to yield at least one product having a stereogenic center.

The term "catalytic amount" is recognized in the art and means a substoichiometric amount of catalyst relative to a reactant. As used herein, a catalytic amount means from 0.0001 to 90 mole percent catalyst relative to a reactant, more preferably from 0.001 to 50 mole percent, still more preferably from 0.01 to 10 mole percent, and even more preferably from 0.1 to 5 mole percent catalyst to reactant.

A "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

An "enantioselective reaction" is a reaction that converts an achiral reactant to a chiral, nonracemic product that is enriched in one enantiomer. Enatioselectivity is generally quantified in terms of "enantiomeric excess" ("e.e."), defined as:

$$e.e. = \left[\frac{(A-B)}{(A+B)}\right] \times 100$$

where A and B are the amounts of enantiomers formed. An enantioselective reaction yields a product with an e.e. greater than zero. Preferred enantioselective reactions yield an e.e. greater than 20%, more preferably greater than 50%, even more preferably greater than 70% and most preferably greater than 80%.

As used herein in reference to a stereoisomerically enriched product, the term "degradation" means a decrease in the yield or the enantiomeric excess of the product.

A "diastereoselective reaction" converts a chiral reactant (which may be racemic or enantiomerically pure) to a product enriched in one diastereomer.

If a chiral reactant is racemic, in the presence of a chiral non-racemic reagent or catalyst, one reactant enantiomer may react more slowly then the other. This is termed a "kinetic resolution", wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A "regioselective reaction" is a reaction which occurs preferentially at one reactive center rather than another reactive center. For example, a regioselective reaction of an unsymmetrically substituted epoxide substrate would cause preferential reaction at one of the two epoxide ring carbons.

The term "non-racemic" with respect to the chiral catalyst, means a preparation of catalyst having greater than 50% of a desired stereoisomer, more preferably at least 75%. "Substantially non-racemic" refers to preparations of the catalyst which have greater than 90% e.e. for a desired stereoisomer of the catalyst, more preferably greater than 95% e.e.

For purposes of this invention, the chemical elements are identified in accordance with the Periodic Table of the Elements, CAS version, Handbook of Chemistry and Physics, 67$^{th}$ Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "alkyl" refers to the radical of saturated aliphatic groups, including straight-chain alkyl groups, branched chain alkyl groups, cycloalkyl (alicyclic) groups, alkyl substituted cycloalkly groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer carbon atoms in its backbone. Likewise, preferred cycloalkyls have from 4 to 10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl, an alkoxyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple bond respectively.

As used herein, "nitro" means —$NO_2$, "halo" means —F, —Cl, —Br or —I, "hydroxyl" means —OH, "carboxyl" means —COOH, "aldehyde" means —C(O)H, and "thio" means —SH, wherein, in each case, R is H, alkyl or aryl, and the term "organometallic" refers to a metallic atom such as mercury, zinc, lead, magnesium or lithium) or a metalloid (such as silicon, arsenic or selenium) which is bonded directly to a carbon atom, such as a diphenylmethoylsilyl group.

Thus, the term "alkylamine" as used herein means an alkyl group, as defined above, having a substituted or unsubstituted amine attached thereto. In exemplary embodiments, an "amine" can be represented by the general formula:

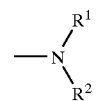

wherein $R^1$ and $R^2$ each independently represent a hydrogen, an alkyl, an alkenyl, —$(CH_2)_m$—$R^3$—C(=O)-alkyl, —C(=O)—alkenyl, —C(=O)-alkynyl, —C(=O)—$(CH_2)_m R^3$, or $R^1$ and $R^2$ taken together with the N atom to which they are attached complete a heterocycle having from 4 to 8 atoms in the ring structure; $R^3$ represents an aryl, a cycloalkyl, a cycloalkenyl, a heterocycle or a polycycle; and m is zero or an integer in the range of 1 to 8.

"Amido" means a substituent group according to the general formula:

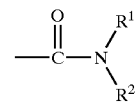

wherein $R^1$ and $R^2$ are as defined above.

"Imino" means a substituent group the general formula:

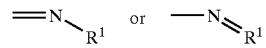

wherein $R^1$ is as described above, with the added proviso that $R^1$ cannot be H.

"Thioether" means a moiety represented by one of —S-alkyl, —S-alkenyl, —S-alkynyl, and —S—$(CH_2)_m R^3$, wherein m and $R^3$ are defined above.

The term "carbonyl" means —C(O)—. The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

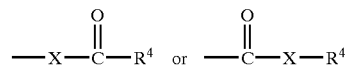

wherein X is absent or represents an oxygen or a sulfur, and $R^4$ represents a hydrogen, an alkyl, an alkenyl, or —$(CH_2)_m R^3$, where m and $R^3$ are as defined above. Where X is an oxygen, the formula represents an "ester". Where X is sulfur, the formula represents a "thioester". Where X is absent, and R⁴ is not hydrogen, the above formula represents a "ketone" group. Where the oxygen atom of the above formula is replace by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of -O-alkyl, -O-alkenyl, O-alkynyl, —O—(CH$_2$)$_m$—R³ where m and R³, are described above.

"Phosphoryl" can in general be represented by the formula:

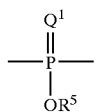

wherein Q¹ represented S or O, and R⁵ represents hydrogen, a lower alkyl or an aryl. When used to substitute an alkyl, the phosphoryl group of the phosphorylalkyl can be represented by the general formula:

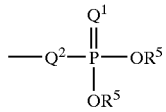

wherein Q¹ represented S or O, and each R⁵ independently represents hydrogen, a lower alkyl or an aryl, Q² represents O, S or N.

As used herein the term "phosphino" includes —PR$_2$ and the term "phosphonato" means —P(OR)$_2$, wherein R is H, alkyl, aryl, heterocyclic or polycyclic.

In a preferred embodiment, the "silyl" moiety which may be substituted on the alkyl can be represented by the general formula:

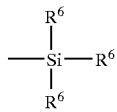

wherein each R⁶ independently represents a hydrogen, an alkyl, an alkenyl, or —(CH$_2$)$_m$—R³, wherein m and R³ defined as above.

Exemplary "selenoethers" which may be substituted on the alkyl are selected from one of —Se—(CH$_2$)$_m$—R³, wherein m and R³ are defined as above.

The term "sulfonyl" as used herein means a S(O)$_2$ moiety bonded to two carbon atoms and the term "sulfonate" as used herein means a sulfonyl group, as defined above, attached to an alkoxy, aryloxy or hydroxy group. Thus, in a preferred embodiment, a sulfonate has the structure:

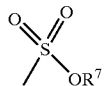

wherein R⁷ is H, alkyl or aryl.

The term sulfate, as used herein, means a sulfonyl group, as defined above, attached to a hydroxy or alkoxy group. Thus, in a preferred embodiment, a sulfate has the structure:

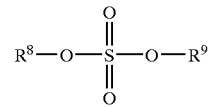

wherein R⁸ and R⁹ are independently absent, a hydrogen, an alkyl, or an aryl. Furthermore, R⁸ and R⁹ taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkyleneimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiopene, imidazole, oxazole, thiazole, triazole, pyrazole, pyridine, pyrazine, pyridazine and pyrimidine, and the like. Those aryl groups having heteroatoms in the ring positions may be substituted with such substituents as described above, for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R³, —CF$_3$, —CN, or the like, wherein m and R³ are defined as above.

The term "heteroatom" as used herein means an atom of any element other than carbon or hydrogen. Preferred heteroatoms are nitrogen, oxygen, sulfur, phosphorus and selenium.

The terms "heterocycle" or "heterocyclic group" refer to 3 to 10-membered ring structures, more typically 5 to 7-membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, adehydes, esters, or —(CH$_2$)$_m$R³, —CF$_3$, —CN, or the like, wherein m and R³ are defined as above.

The term "carbocycle" refers generally to ring structures wherein the ring members are each carbon atoms.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, adehydes, esters, or —(CH$_2$)$_m$R³, —CF$_3$, —CN, or the like, wherein m and R³ are defined as above.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R^{10}$—$R^{11}$—$R^{12}$—, wherein $R^{10}$ and $R^{12}$ are each independently absent or represent an alkyl, an alkenyl, or an alkynyl, each preferably $C_1$ to $C_{10}$, and $R^{11}$ is absent or represents an amine, an imine, an amide, a phosphoryl, a carbonyl, a silyl, an oxygen, a sulfonyl, a sulfur, a selenium, or an ester.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds, illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

As used herein in reference to a catalyst complex, "crystalline solid form" means that the complex is a solid, typically particulate, material that, upon visual examination, exhibits a regular, repeating structural pattern. The visual examination may be macroscopic or microscopic. While not wishing to be bound by theory, it is believed that such crystalline solid form is a manifestation of having the molecules of the complex arranged in a lattice structure.

As used herein, the term "flashpoint" means the temperature at which a liquid gives off vapor sufficient to form ignitable mixtures with air, as determined according to any applicable "closed cup" or "open cup" test method, such, for example, according to the Tagliabue open cup method given in ASTM D1210-63.

Ligands suitable as the asymmetric tetradentate ligand component of the method of the present invention are those derived from, for example, salens, porphyrins, crown ethers, azacrown ethers, cyclams or phthalocyanines. In one embodiment, the tetradentate ligand is derived from a chiral salen or salen-like ligand.

In one embodiment, the asymmetric tetradentate ligand comprises at least one compound according to the structural formula (1) or a salt thereof:

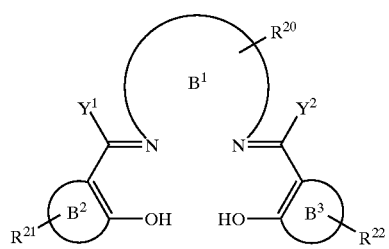

(1)

wherein:
B$^1$ is a bridging subsituent,
B$^2$ and B$^3$ each independently represent a ring moiety comprising from 4 to 8 atoms in its ring structure selected from cycloalkyl, cycloalkenyl, cycloalkenyl, aryl and heterocyclic,
Y$^1$ and Y$^2$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, R$^{20}$, R$^{21}$, R$^{22}$ each represent one or more covalent substitutions of the respective B$^1$, B$^2$, and B$^3$ moieties with H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—R$^{23}$, wherein R$^{20}$ can appear at one or more positions of the bridging moiety B$^1$, R$^{23}$ is aryl, cycloalkyl, cycloalkenyl or heterocyclyl or polycyclyl, and n is zero or an integer of from 1 to 8, provided that the substituents of the ligand of formula (1) are selected such that the ligand is asymmetric.

In a preferred embodiment, the asymmetric tetradentate ligand comprises at least one compound according to the structural formula (2) or a salt thereof:

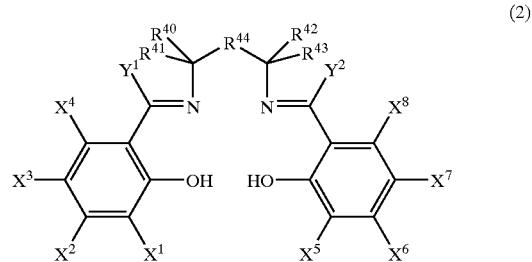

(2)

wherein:
R$^{40}$, R$^{41}$, R$^{42}$, R$^{43}$ R$^{44}$, X$^1$, X$^2$, X$^3$, X$^4$, X$^5$, X$^6$, X$^7$ and X$^8$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—R$^{23}$, or, alternatively, may be fused with another one of the R$^{40}$, R$^{41}$, R$^{42}$, R$^{43}$ R$^{44}$, X$^1$, X$^2$, X$^3$, X$^4$, X$^5$, X$^6$, X$^7$ and X$^8$ substituents to form a carbocyclic or heterocyclic ring structure having from 4 to 8 atoms in its ring structure, provided that R$^{44}$ may be absent, in which case, the carbon atom bearing the R$^{40}$ and R$^{41}$ substituents is covalently bonded to the carbon atom bearing the R$^{42}$ and R$^{43}$ substituents and R$^{40}$ and R$^{41}$ may each independently be fused with one of R$^{42}$ or R$^{43}$ to form a ring structure that includes the carbon atoms to which they are bound, and R$^{23}$, Y$^1$, Y$^2$, and n are each defined as above, further provided that the substituents of the ligand of formula (2) are selected such that the ligand is asymmetric.

In a preferred embodiment, the ligand comprises at least one compound according to structure (2), wherein R$^{44}$ is absent, R$^{40}$ and R$^{42}$ are fused to, together with the carbon atoms to which they are attached, form a 1,2-cyclohexylene group, In a preferred embodiment, the ligand comprises at least one metal-ligand complex according to structure (2), wherein R$^{41}$, R$^{43}$, Y$^1$, Y$^2$, X$^2$, X$^4$, X$^6$ and X$^8$ are each H, and X$^1$, X$^3$, X$^5$ and X$^7$ are each t-butyl.

The Brønsted acid component of the process of the present invention may be any compound that, under the reaction conditions, is capable of donating a proton. In certain embodiments, the Brønsted acid has a flash point of greater than or equal to about 30° C. In certain embodiments, the Brønsted acid has a boiling point of less than or equal to 200° C. In certain embodiments, the Brønsted acid has a flash point of greater than or equal to about 35° C. and a boiling point of less than or equal to 160° C. In a preferred embodiment, the acid is selected from acetic acid, propionic acid, isobutyric acid, trifluoroacetic acid, and methane sulfonic acid. In a preferred embodiment, the Brønsted acid comprises acetic acid.

In one embodiment, the ligand is contacted with from about 5 to about 10 molar equivalents of the Brønsted acid, based on the amount of transition metal.

In another embodiment, as further discussed below, from about 2 to about 10 volumes of the Brønsted acid per unit volume of ligand is used as a liquid medium in which to conduct the catalyst formation.

Suitable Co(II) or Cr(II) salts include, for example, cobalt acetate, cobalt propionate, cobalt isobutyrate, cobalt trifluoroacetate, chromium acetate, chromium propionate, chromium isobutyrate, and chromium trifluoroacetate, each of which may be in anhydrous or hydrated form. In a preferred embodiment, the metal salt comprises cobalt acetate. Cobalt acetate is commercially available as cobalt acetate tetrahydrate.

In one embodiment, the ligand is contacted with from about 1 to about 2 molar equivalents of the metal salt, based on the amount of ligand.

In the case of Cr(II) salts, it is preferred to contact the Cr(II) salt with the ligand and acid under an inert atmosphere prior to contacting with the oxidant in order to allow formation of a Cr(II) ligand complex prior to oxidizing the Cr(II) to Cr(III).

In a preferred embodiment, the oxidant component of the method of the present invention comprises oxygen. In one embodiment, the oxygen is introduced in the form of air. In a preferred embodiment, the ligand, acid and metal salt are contacted with from about 100 about 1000 liters of air per kilogram of ligand per hour. In another preferred embodiment, the ligand, acid and metal salt are contacted with from about 200 about 800 liters of air per kilogram of ligand per hour.

In one embodiment, oxygen is introduced into the catalyst formation reaction mixture by bubbling air into the mixture, for example, though a sparger tube having its outlet end submerged in the mixture The water miscible protic solvent component of the process of the present invention may be any water miscible protic solvent that will not adversely affect the reactants or the catalyst complex and in which the catalyst complex is at least substantially soluble, and from which the catalyst complex can be precipitated by the addition of water. In one embodiment, the solvent is selected from methanol, ethanol, n-propanol and 1-methoxy-2-propanol. As used herein, the statement that a catalyst complex is "substantially soluble" in a solvent means that means that at least one kilogram of the complex dissolves in from about 1 liter to about 20 liters of the solvent. As used here in reference to a solvent, "water miscible" means that the solvent is capable of being mixed with water in any proportion without phase separation.

The step of forming a solution of the catalyst complex in the water miscible protic solvent may be formed simultaneously with the contacting step or subsequent to the contacting step.

In one embodiment, the ligand, acid salt and oxidant are contacted in the water miscible protic solvent to form the solution of the complex in the water miscible protic solvent. In a preferred embodiment, the catalyst complex formation reaction is conducted in from about 2 to about 15 liters of the water miscible protic solvent per kilogram of the ligand.

In another embodiment, the catalyst complex formation reaction is conducted in a liquid reaction medium having a flash point greater than or equal to about 35° C. and a water-miscible protic solvent is exchanged for the liquid reaction medium, for example, by stripping off the liquid reaction medium and adding the water miscible protic solvent. In one embodiment, from about 2 to about 15 liters of the water-miscible protic solvent are added per kilogram of the complex. Suitable liquid reaction media include, for example, an excess of the Brønsted acid.

In a preferred embodiment, the ligand, acid salt and oxidant are contacted in an excess of the Brønsted acid and the solution of complex in the water miscible protic solvent is formed by stripping off the excess Brønsted acid and adding the water-miscible protic solvent. In a preferred embodiment, form about 2 to about 15 liters of the water miscible protic solvent is added per kilogram of the ligand.

In general, the catalyst formation process is run under mild conditions that will not adversely affect the reactants, catalyst or product, such as for example, a temperature of from about −20° C. to about 200° C., more preferably from about 25° C. to about 150° C.

In a preferred embodiment, any activity involving a material having a flash point below about 35° C., for example, formation of a solution of the complex in certain water-miscible, protic solvents, is conducted under an inert atmosphere, such as, for example, under an argon or nitrogen atmosphere.

In a preferred embodiment, from about 0.5 to about 5 volumes of water per unit volume of the solution of catalyst complex in the water miscible protic solvent is added to the solution to precipitate the complex.

In certain embodiments, the catalyst complex precipitates in the form of a crystalline solid. In certain embodiments, the solution of catalyst complex is seeded, for example, by adding crystals of the catalyst complex to a mixture of the solution and water, to encourage crystallization of the catalyst complex from the solution. In the absence of seeding, precipitated crystals of catalyst complex typically exhibit a relatively small particle size, such as for example, from about 10 to about 25 micrometers ($\mu$m). The relatively small crystals so formed are suitable for use as a catalyst for stereoselective ring opening reactions or as seed particles in subsequent precipitations of catalyst complex. Particles of catalyst complex having a particle size of greater than 25 $\mu$m are also suitable as seed particles. Typically, from about 0.5 to about 2.0 percent by weight (wt %) seed particles, based on the anticipated total amount of catalyst complex to be crystallized, are added to the mixture of the solution and water. The introduction of seed particles encourages formation of crystalline particles of isolated catalyst complex having a particle size greater than that of the seed crystals. In certain embodiments, increased particle size of catalyst complex crystals offers advantages with regard to improving the ease of the subsequent processing the crystals, including improved ease of isolation of the crystals by filtration and improved ease of drying the isolated crystals. As used here, the term "particle size" refers to the apparent length of the longest dimension of a particle, measured, for example, by visually comparing the dimension to a scale provided in a reticle of an optical microscope.

In a preferred embodiment, the precipitated complex is then isolated, for example, by filtration.

In a preferred embodiment, the isolated catalyst complex is washed with a suitable washing liquid, preferably water, isolated from the washing liquid, and then dried, for example, under vacuum, to yield catalyst complex in particulate solid form. Suitable washing and isolation techniques include displacement washing, that is, directing a washing liquid through a bed or filter cake of the isolated complex, and slurry washing, that is, mixing slurry of the catalyst complex and a washing liquid, and then filtering the slurry.

The isolated catalyst complex is then dried, for example, at slightly elevated temperature, for example, from about 30 to about 60° C., or under reduced pressure, for example, less than about 500 millibars, or under elevated temperature and reduced pressure. Preferably, the isolated catalyst complex is dried to constant weight, that is, until further drying of the isolated catalyst produces no further loss of weight.

In certain embodiments, the dried active catalyst complex is then stored in closed containers that are at least substantially impervious to moisture and air. Isolated catalyst has been found to retain its activity in catalyzing stereoselective ring opening reactions during prolonged storage. It is believed that thorough drying and preventing contact of the isolated complex with moisture during storage enhance the stability of the active catalyst.

The ability to isolate the active catalyst complex as a dry, free flowing stable solid material allows for improved ease of analytical characterization, and performance testing of the active catalyst complex and for greater batch-to-batch reproducibility in the ring-opening reactions in which such active catalyst complex is used.

In known Co(III)-salen ligand catalyst complex activation methods, active catalyst is formed on a reaction-by-reaction basis in the reactor to be used in the stereoselective ring opening reaction, typically before the addition of the reactants, i.e., the nucleophile and substrate compounds, and catalyst performance data are not typically obtained prior to use in the stereoselective ring opening reaction. The active catalyst can now be produced according to the method of the present invention in larger batches rather than on a reaction-by-reaction basis, which leads to greater reproducibility and reliability in the use of the catalyst.

The method of the current invention requires less time than known in situ Co(III)salen ligand catalyst complex activation processes, and provides a significant environmental advantage compared to such processes in that the method eliminates the need to use chlorinated solvents, such as, for example, methylene chloride.

In one embodiment, the catalyst complex of the present invention comprises at least one complex according to structural formula (3):

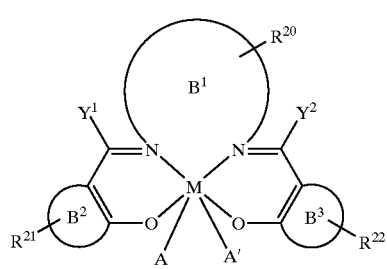

(3)

wherein $B^1$, $B^2$, $B^3$, $R^{20}$, $R^{21}$, $R^{22}$, $Y^1$ and $Y^2$ are each defined as above and are selected such that the complex is asymmetric, M is Co(III) or Cr(III), A is a counterion or nucleophile, and A' is absent or is a molecule of water, a protic, water miscible solvent or a Brønsted acid.

Counterions and nucleophiles suitable as the A substituent of the complex include, for example, carboxylates, hydroxide, alkoxides, thiolates, sulfonates, phenoxides, sulfonamides, azide, isocyanate, isothiocyanate, and halides. In a preferred embodiment, A is selected from acetate, 4-nitrobenzoate, and (1S)-10-camphorsulfonate.

In a preferred embodiment, A' is a molecule of methanol.

In a preferred embodiment, the chiral catalyst comprises at least one complex according to the structural formula (4):

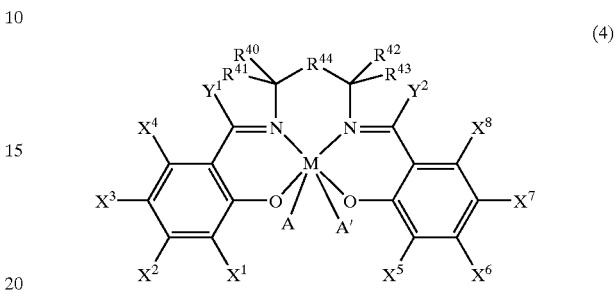

(4)

wherein $R^{40}$, $R^{41}$, $R^{42}$, $R^{43}$, $R^{44}$, $Y^1$, $Y^2$, $X^1$, $X^2$, $X^3$, $X^4$, $X^5$, $X^6$, $X^7$ and $X^8$ M, A and A' are each defined as above and are selected such that the complex is asymmetric.

In one embodiment, the chiral catalyst of the present invention has a rectangular planar or rectangular pyramidal geometry.

In a preferred embodiment, the chiral catalyst comprises at least one metal-ligand complex according to structure (4), wherein $R^{44}$ is absent, $R^{40}$ and $R^{42}$ are fused to, together with the carbon atoms to which they are attached, form a 1,2-cyclohexylene group.

In a preferred embodiment, the chiral catalyst comprises at least one metal-ligand complex according to structure (4), wherein $R^{41}$ and $R^{43}$, $Y^1$, $Y^2$, $X^2$, $X^4$, $X^6$ and $X^8$ are each H, and $X^1$, $X^3$, $X^5$ and $X^7$ are each t-butyl.

In one preferred embodiment, the chiral catalyst comprises at least one metal-ligand complex according to structure (4), wherein M is Co(II). By isolating the active Co(III) catalyst, synthesis and isolation of the inactive Co(II) catalyst is precluded, which results in significant cost savings.

In certain embodiments, the catalyst complex is precipitated and isolated in crystalline solid form. In certain embodiments, the catalyst complex is isolated as free flowing crystalline solid particles having a particle size of from about 10 to about 1000 μm, more typically from about 25 to about 200 μm.

In certain preferred embodiments, the isolated catalyst complex is stable, that is, the catalyst retains its activity, during storage for greater than or equal to about 3 months, more preferably greater than or equal to about 6 months, under ambient conditions in closed containers.

The active catalyst formed by the method of the present invention is useful as a catalyst for catalyzing stereoselective ring opening reactions of cyclic substrates with nucleophiles and eliminates the need to conduct the catalyst activation in the same reactor as the ring-opening reaction while generally performing at least as well as similar catalysts prepared by such in situ methods.

In general, any chemical compound having a reactive pair of electrons is suitable as the nucleophile of the stereoselective ring opening reaction. Compounds that, under appropriate reaction conditions, are suitable for use as the nucleophile in the method of the present invention include, for example, hydride; uncharged compounds such as amines, mercaptans, and alcohols, including phenols; charged compounds such as alkoxides, phenoxides, thiolates; organic or inorganic anions, such as carbanions, azide, cyanide, thiocyanate, acetate, formate, chloroformate and bisulfite anions; organometallic reagents such as organocuprates, organozincs, organolithiums, Grignard reagents, enolates and acetylides.

In a more highly preferred embodiment, the nucleophile comprises one or more compounds selected from water, phenoxides, hydroxides, alkoxides, alcohols, thiols, thiolates, carboxylic acids and carboxylates, and, even more preferably, from water, phenols, particularly silyated phenols, and carboxylic acids.

In a preferred embodiment, the cyclic substrate of the stereoselective ring opening reaction comprises a compound according to formula (5):

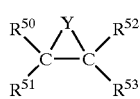

(5)

wherein:

$R^{50}$, $R^{51}$, $R^{52}$ and $R^{53}$ are each independently an organic or inorganic substituent which form a covalent bond with the carbon atom to which it is attached and which permit the formation of a stable ring structure including Y, and Y is O, S, —$NR^{54}$, —$C(R^{55})R^{56}$, or has the formula G—H—I, wherein $R^{54}$ is H, alkyl, carbonyl-substituted alkyl, carbonyl-substituted aryl or sulfonate, $R^{55}$ and $R^{56}$ are each independently an electron withdrawing group, G and I are each independently absent or ($C_1$-$C_5$)alkyl, O, S, carbonyl or —$NR^{54}$, and H is carbonyl, phosphoryl or sulfonyl.

In a preferred embodiment, $R^{50}$, $R^{51}$, $R^{52}$ and $R^{53}$ are each independently H, hydroxyl, halo, alkyl, alkenyl, alkynyl, amino, imino, amido, nitro, thio, phosphoryl, phosphonato, phosphino, carbonyl, carboxyl, silyl, sulfonyl, or a ketone, aldehyde, ester, thioether, selenoether, or —$(CH2)_nR^{57}$, wherein $R^{57}$ is aryl, cycloalkyl, cycloalkenyl or heterocyclyl and n is a number wherein $0 \leq n \leq 8$, or may alternatively, be fused with another one of the $R^{50}$, $R^{51}$, $R^{52}$ or $R^{53}$ substituents to form, together with the carbon atoms to which such substituents are attached, a carbocyclic or heterocyclic ring structure.

In a more highly preferred embodiment, the substrate comprises a cyclic compound containing a electrophilic center and a leaving group, including, for example, epoxides, such as epichlorohydrin, aziridines, such as 1,2-propylene imine, episulfides, such as 1,2-propylene sulfide, cyclic carbonates, such as 1,2-propylene glycol cyclic carbonate, cyclic thiocarbonates, such as 1,2-propylene glycol cyclic thiocarbonate, cyclic phosphates, such as 1,2-propylene glycol cyclic phosphate, cyclic sulfates, such as 1,2-propylene glycol cyclic sulfate, cyclic sulfites, such as 1,2, propylene glycol cyclic sulfite, lactams, such as β-butyrolactam, thiolactams, such as β-butyrothiolactam, lactones, such as β-methyl-γ-butyrolactone, thiolactones, such as β-methyl-γ-butyrothiolactone, and sultones, such as 1,3-butyrosultone.

In general, the stereoselective ring opening reaction is conducted under mild conditions that will not adversely affect the reactants, catalyst or product, such as for example, a temperature of from about −20° C. to about 200° C., more preferably from about 25° C. to about 150° C.

In general, the stereoselective ring opening reaction is conducted in a liquid reaction medium. The reaction may be conducted without additional solvent, in an inert solvent, such as one or more of benzene, toluene, tetrahydrofuran, dichloromethane, hexane, dimethylsulfoxide or in a reactive solvent, such as for example, using ethanol as both a nucleophile and a solvent.

In certain embodiments, the stereoselective ring opening reaction is conducted in an inert atmosphere, such as, for example, under an argon or nitrogen atmosphere. Alternatively, the reaction may be conducted under a reactive atmosphere, such as, for example, conducting ring opening an epoxide cyanide nucleophile under HCN gas.

EXAMPLE 1

An active catalyst was made by reacting a chiral salen ligand, $Co(OAc)_2 \cdot 4H_2O$, acetic acid, and air in methanol according to the following scheme:

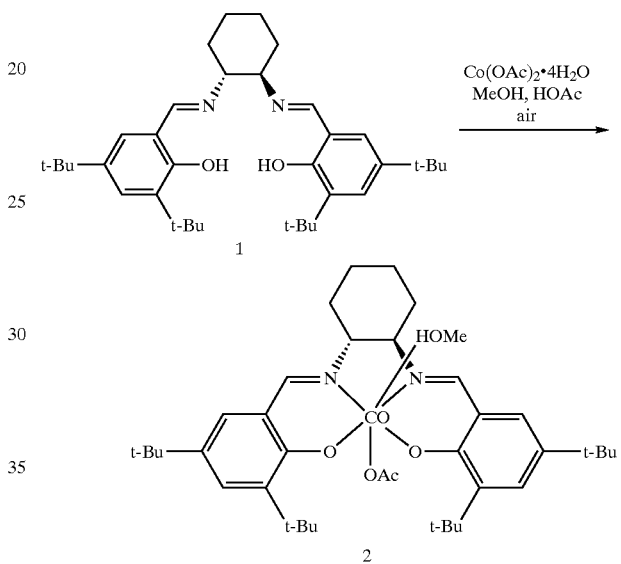

(R,R)-Jacobsen's ligand 1 (82 g, 0.15 mol, 1.0 equiv) was charged to a 3-L, 3-neck round bottom flask equipped w/mechanical stirrer, thermometer, and air-sparging dip tube. MeOH (750 mL) was then charged to the vessel at ambient temperature. Glacial Acetic Acid (18 g, 0.3 mol, 2.0 equiv) was then charged to the flask. $Co(OAc)_2 \cdot 4H_2O$ (41.9 g, 0.165 mol, 1.1 equiv) was charged to the reaction vessel and an additional 75 mL MeOH (approx. 10 volumes total) was used as a rinse. The contents of the flask were stirred open to the air for 30 minutes until most of the ligand solids had dissolved. Then, an air stream was pulled through the dark green/brown mixture via house vacuum using a dip tube open to the atmosphere with stirring for 2 hours. The contents of the flask were monitored for consumption of ligand and absence of Co(II)salen catalyst by TLC. When monitoring indicated completion of the reaction, the sparge tube was replaced with an addition funnel and water (850 mL) was slowly added over 2–3 hours (slowly at first, portionwise) via the addition funnel to precipitate the active Co(III) ligand catalyst complex 2. Brown solids were isolated by vacuum filtration of the contents of the reaction vessel through Whatman 3 paper on a Buchner funnel. The solids were washed with water (2×350 mL) and air dried. The solids were scraped off of the filter paper and dried in a vacuum oven at 35° C. under house vacuum to yield 105 g (quantitative) of a dark brown solid, identified by NMR analysis as Co(III) ligand catalyst complex 2. The NMR spectrum was consistent with the expected complex containing a molecule of methanol coordinated to cobalt, thereby filling the metal's sixth coordination site.

EXAMPLE 2

An active catalyst was made by reacting a chiral salen ligand, $Co(OAc)_2 \cdot 4H_2O$, acetic acid, and air in excess acetic acid according to the following scheme:

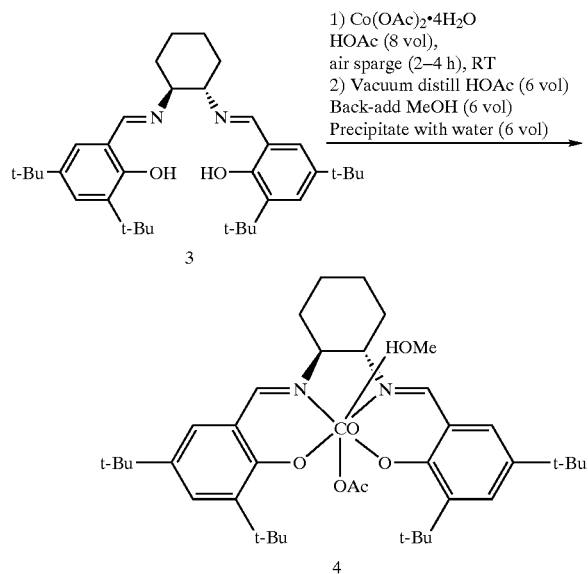

(S,S)-Jacobsen's ligand 3 (2.2 kg) was charged to a reaction vessel equipped with an impeller, thermometer, and air-sparging dip tube. Cobalt acetate tetrahydrate (1.06 kg) was charged to the reaction vessel via charge hole. The reaction vessel was purged with nitrogen. Acetic acid 18.5 kg was charged to the reactor over a period of about 0.5 hr under agitation at room temperature. The contents of the reaction vessel were stirred at room temperature while bubbling with compressed air at a rate of about 750 litres of air/Kg of ligand/hour, through the mixture for 3 hours. The effluent air stream was passed through a sodium hydroxide scrubber. The composition of the contents of the vessel was monitored every 30 minutes by TLC. Upon completion of he reaction (>95% conversion), the air bubbling was discontinued, the vessel was purged with nitrogen and the pressure within the vessel was slowly reduce to 100–110 mbar. The contents of the vessel were then heated for 2–3 h at a pot temperature 50–55° C. and jacket temperature 70° C. and 14 kg of AcOH (75% of the volume used) were stripped of the contents of the reaction vessel. The vacuum was then broken to nitrogen and the contents of the vessel were cooled to room temperature over 0.5–1 h. Methanol (10.5 kg) was then charged to the reaction vessel (the quantity of methanol was equivalent to the volume of removed AcOH). Water (11 kg) was continuously added dropwise, with stirring, over 1.5 hours to precipitate the catalyst. After 10% addition of the water, the reaction was seeded with 25 g seed crystals. The resulting slurry was transferred into a GUEDU filtration still. Pressure was applied to isolate the solid. The isolated solid was washed by adding water (~50 kg, in total) by portion until a clear filtrate solution was obtained. The filtrate solution had a pH between 3.5 and 4.5. The washed isolated solid was dried in a vacuum oven (40° C., 35 mmbar) to constant weight to yield 2.8 kg solid (95–97% of theoretical), identified by NMR analysis as Co(III) ligand catalyst complex 4.

EXAMPLE 3

The stability of the catalyst was evaluated by monitoring the activity of the catalyst in the hydrolytic kinetic resolution ("HKR") of racemic epichlorohydrin versus the length of time the isolated catalyst had been stored in a closed container at ambient temperature.

To a 125-mL jacketed vessel equipped with an overhead mechanical stirrer and a thermometer was added a (R,R)-Co(III)-salen ligand-acetate-methanol catalyst complex made according the procedure given in Example 1 above (1.66 g, 2.5 mmol, 0.5 mol % with respect to racemic epoxide). Racemic epichlorohydrin (46.7 g, 0.5 mol) was added to the vessel, and the mixture was brought to 5° C. with a temperature-controlled recirculating fluid. Water (6.75 g, 0.375 mol, 0.75 equiv with respect to racemic epoxide) was charged over a period of 2 hours using a syringe pump. Upon complete addition, the reaction was monitored by chiral GC analysis until completion as indicated by epichlorohydrin enantiomeric excess >99%.

HKR reactions were conducted according to the above procedure at various times using samples of the stored catalyst complex. The results obtained using catalyst complex stored for different lengths of time ("Storage Time", expressed in months, are set forth below in TABLE I, in terms of the enantiomeric excess of the epichlorohydrin product obtained ("Epichlorohydrin e.e.", expressed as a percent, and the reaction time, expressed in hours, required to reach the reported e.e. value for the reaction ("Reaction Time").

TABLE I

| Storage Time (months) | Epichlorohydrin ee (%) | Reaction Time |
|---|---|---|
| 0 | 100% | 4 h 40 min |
| 2 | 99.5% | 5 h 16 min |
| 7 | 99.5% | 5 h 00 min |

Analogous results are provided in TABLE II below for HKR of epichlorohydrin conducted with samples of a stored (S,S)-Co(III)-salen ligand-acetate-methanol catalyst complex that had been made according to the procedure given in Example 2 above.

TABLE II

| Storage Time (months) | Epichlorohydrin ee (%) | Reaction Time |
|---|---|---|
| 0 | 99.1% | 4 h 00 min |
| 3 | 99.6% | 5 h 36 min |

What is claimed is:

1. A method for making a chiral catalyst complex, comprising:

contacting an asymmetric tetradentate ligand with a Brønsted acid, a Co(II) or Cr(II) salt, wherein the acidity of the conjugate acid of the salt is the same as or less than the acidity of the Brønsted acid, and an oxidant under conditions effective to allow formation of a chiral catalyst complex of Co(III) or Cr(III) and the ligand, forming a solution of the complex in a water-miscible, protic solvent from which the complex can be precipitated by the addition of water, and adding water to the solution to precipitate at least a portion of the complex.

2. The method of claim 1, wherein the asymmetric tetradentate ligand comprises at least one compound according to the structural formula (1) or a salt thereof:

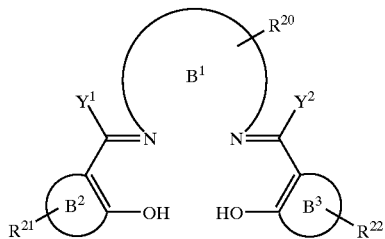

(1)

wherein:

$B^1$ is a bridging subsituent —$R^{10}$—$R^{11}$—$R^{12}$—, wherein $R^{10}$ and $R^{12}$ are each independently absent or represent an alkyl, an alkenyl, or an alkynyl, and $R^{11}$ is absent or represents an amine, an imine, an amide, a phosphoryl, a carbonyl, a silyl, an oxygen, a sulfonyl, a sulfur, a selenium, or an ester, $B^2$ and $B^3$ each independently represent a ring moiety comprising from 4 to 8 atoms in its ring structure selected from cycloalkyl, cycloalkenyl, cycloalkenyl, aryl and heterocyclic.

$Y^1$ and $Y^2$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$.

$R^{20}$, $R^{21}$, $R^{22}$ each represent one or more covalent substitutions of the respective $B^1$, $B^2$, and $B^3$ moieties with H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, wherein $R^{20}$ can appear at one or more positions of the bridging moiety $B^1$, $R^{23}$ is aryl, cycloalkyl, cycloalkenyl or heterocyclyl or polycyclyl, and n is zero or an integer of from 1 to 8, provided that the substituents of the ligand of formula (1) are selected such that the ligand is asymmetric.

3. The method of claim 1, wherein the asymmetric tetradentate ligand comprises art least one compound according to the structural formula (2) or a salt thereof:

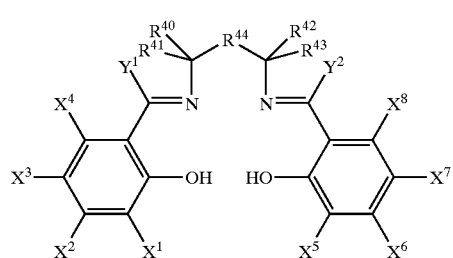

(2)

wherein:

$R^{40}$, $R^{41}$, $R^{42}$, $R^{43}$, X1, $X^2$, $X^3$, $X^4$, $X^5$, $X^6$, $X^7$ and $X^8$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, or, alternatively, may be fused with another one of the $R^{40}$, $R^{41}$, $R^{42}$, $R^{43}$, $X^1$, $X^2$, $X^3$, $X^4$, $X^5$, $X^6$, $X^7$ and $X^8$ substituents to form a carbocyclic or heterocyclic ring structure having from 4 to 8 atoms in its ring structure, $R^{44}$ is absent and the carbon atom bearing the $R^{40}$ and $R^{41}$ substituents is covalently bonded to the carbon atom bearing the $R^{42}$ and $R^{43}$ substituents and $R^{40}$ and $R^{41}$ may each independently be fused with one of $R^{42}$ or $R^{43}$ to form a ring structure that includes the carbon atoms to which they are bound, $Y^1$ and $Y^2$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, $R^{23}$ is aryl, cycloalkyl, cycloalkenyl or heterocyclyl or polycyclyl, and n is zero or an integer of from 1 to 8, further provided that the substituents of the ligand of formula (2) are selected such that the ligand is asymmetric.

4. The method of claim 3, wherein $R^{40}$ and $R^{42}$ are fused to, together with the carbon atoms to which they are attached, form a 1,2-cyclohexylene group.

5. The method of claim 3, wherein $R^{41}$, $R^{43}$, $Y^1$, $Y^2$, $X^2$, $X^4$, $X^6$ and $X^8$ are each H, and $X^1$, $X^3$, $X^5$ and $X^7$ are each t-butyl.

6. The method of claim 1, wherein the Brønsted acid has a flash point of greater than or equal to about 30° C.

7. The method of claim 1, wherein the Brønsted acid the acid comprises a compound selected from acetic acid, propionic acid, isobutyric acid, trifluoroacetic acid, and methane sulfonic acid.

8. The method of claim 1, wherein the salt comprises a compound selected from cobalt acetate, cobalt propionate, cobalt isobutyrate, cobalt trifluoroacetate, chromium acetate, chromium propionate, chromium isobutyrate and chromium trifluoroacetate, each of which may be in anhydrous or hydrated form.

9. The method of claim 1, wherein the oxidant comprises oxygen.

10. The method of claim 9, wherein the oxygen is introduced in the form of air.

11. The method of claim 1, wherein the water miscible protic solvent comprises a compound selected from methanol, ethanol, n-propanol, and 1-methoxy-2-propanol.

12. The method of claim 1, wherein the ligand, acid salt and oxidant are contacted in the water miscible protic solvent to form the solution of the complex in the water-miscible protic solvent.

13. The method of claim 1, wherein the ligand, acid salt and oxidant are contacted in a liquid reaction medium having a flash point greater than or equal to about 35° C. and the solution of the complex in the water-miscible protic solvent is formed by exchanging the water-miscible protic solvent for the liquid reaction medium.

14. The method of claim 1, wherein seed particles comprising crystalline particles of the catalyst complex are added to the solution prior to or during the step of adding water to the solution.

15. The method of claim 14, wherein the seed particles have a particle size of from about 10 to about 25 micrometers.

16. The method of claim 14, wherein seed particles are added to the solution in an amount of from about 0.5 to about 2 percent by weight of seed particles, based on the total weight of catalyst complex to be precipitated.

17. The method of claim 1, wherein the precipitated complex is isolated by filtration.

18. A method of making chiral catalyst complex, comprising:

contacting an asymmetric tetradentate ligand according to the structural formula (2) or a salt thereof

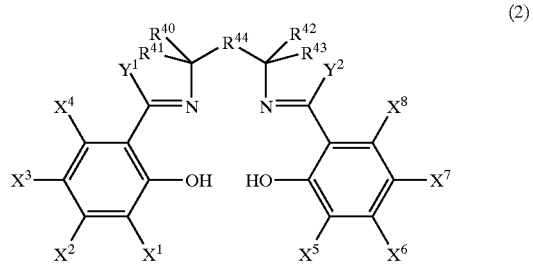

(2)

wherein:

$R^{40}, R^{41}, R^{42}, R^{43}$, X1, $X^2, X^3, X^4, X^5, X^6, X^7$ and $X^8$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, or, alternatively, may be fused with another one of the $R^{40}, R^{41}, R^{42}, R^{43}, X^1, X^2, X^3, X^4, X^5, X^6, X^7$ and $X^8$ substituents to form a carbocyclic or heterocyclic ring structure having from 4 to 8 atoms in its ring structure, $R^{44}$ is absent and the carbon atom bearing the $R^{40}$ and $R^{41}$ substituents is covalently bonded to the carbon atom bearing the $R^{42}$ and $R^{43}$ substituents and $R^{40}$ and $R^{41}$ may each independently be fused with one of $R^{42}$ or $R^{43}$ to form a ring structure that includes the carbon atoms to which they are bound, $Y^1$ and $Y^2$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, $R^{23}$ is aryl, cycloalkyl, cycloalkenyl or heterocyclyl or polycyclyl, and n is zero or an integer of from 1 to 8, further provided that the substituents of the ligand of formula (2) are selected such that the ligand is asymmetric, with a Brønsted acid selected from acetic acid, propionic acid, isobutyric acid, trifluoroacetic acid, and methane sulfonic acid, a Co(II) or Cr(II) salt selected from cobalt acetate, cobalt propionate, cobalt isobutyrate, cobalt trifluoroacetate, chromium acetate, chromium propionate, chromium isobutyrate and chromium trifluoroacetate, and air under conditions effective to allow formation of a chiral catalyst complex of Co(III) or Cr(III) and the ligand forming a solution of the complex in a water-miscible, protic solvent comprising a compound selected from methanol, ethanol and n-propanol, and adding water to the solution to precipitate at least a portion of the complex.

19. The method of claim 18, wherein the ligand, acid salt and oxidant are contacted in the water miscible protic solvent to form the solution of the complex in the water miscible protic solvent.

20. The method of claim 18, wherein the ligand, acid salt and oxidant are contacted in an excess of the Brønsted acid and the solution of complex in the water miscible protic solvent is formed by exchanging the water-miscible protic solvent for the excess of the Brønsted acid.

21. A method for making a chiral catalyst complex in particulate solid form, comprising:

providing a solution of a chiral catalyst complex of Co(III) or Cr(III) with an asymmetric tetradentate ligand in a water-miscible, protic solvent comprising a compound selected from methanol, ethanol, n-propanol and 1-methoxy-2-propanol, adding water to the solution to precipitate at least a portion of the complex, and isolating the precipitated complex as a particulate solid.

22. A catalyst active in catalyzing stereoselective ring opening reactions, comprising a chiral catalyst complex of Co(III) or Cr(III) with an asymmetric tetradentate ligand and a counterion or nucleophile selected from carboxylate, hydroxide, alkoxide, thiolate, sulfonate, sulfonamide, isocyanate, isothiocyanate, and halide, wherein the complex is in crystalline solid form, wherein at least one molecule of the chiral catalyst complex further comprises a molecule of methanol.

23. The catalyst of claim 22, wherein the chiral catalyst complex has a rectangular planar or rectangular pyramidal geometry.

24. The catalyst claim 22, wherein the catalyst comprises at least one chiral catalyst complex according to structural formula (3):

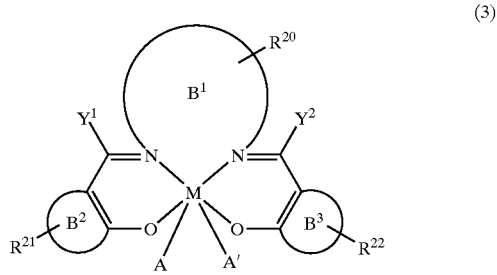

(3)

wherein $B^1$ is a bridging subsituent —$R^{10}$—$R^{11}$—$R^{12}$—, wherein $R^{10}$ and $R^{12}$ are each independently absent or represent an alkyl, an alkenyl, or an alkynyl, and $R^{11}$ is absent or represents an amine, an imine, an amide, a phosphoryl, a carbonyl, a silyl, an oxygen, a sulfonyl, a sulfur, a selenium, or an ester, each $B^2, B^3$ is independently a ring moiety comprising from 4 to 8 atoms in its ring structure selected from cycloalkyl, cycloalkenyl, cycloalkenyl, aryl and heterocyclic, $Y^1$ and $Y^2$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, $R^{20}, R^{21}, R^{22}$ each represent one or more covalent substitutions of the respective $B^1, B^2$, and $B^3$ moieties with H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, wherein $R^{20}$ can appear at one or more positions of the bridging moiety $B^1$, $R^{23}$ is aryl, cycloalkyl, cycloalkenyl or heterocyclyl or polycyclyl, and n is zero or an integer of from 1 to 8, provided that the substituents of the complex of formula (3) are selected such that the complex is asymmetric, M is Co(III) or Cr(III), A is a counterion or nucleophile selected from carboxylate, hydroxide, alkoxide, thiolate, sulfonate, sulfonamide, isocyanate, isothiocyanate, and halide, and A' is a molecule of methanol.

25. The catalyst of claim 22, wherein the catalyst comprises at least one chiral catalyst complex according to structural formula (4):

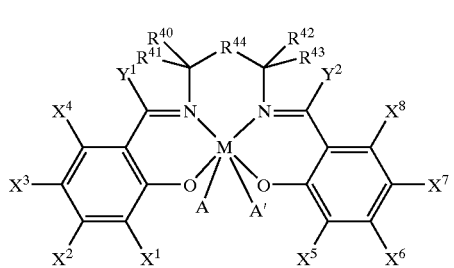

wherein:

$R^{40}$, $R^{41}$, $R^{42}$, $R^{43}$, X1, $X^2$, $X^3$, $X^4$, $X^5$, $X^6$, $X^7$ and $X^8$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, or, alternatively, may be fused with another one of the $R^{40}$, $R^{41}$, $R^{42}$, $R^{43}$, $X^1$, $X^2$, $X^3$, $X^4$, $X^5$, $X^6$, $X^7$ and $X^8$ substituents to form a carbocyclic or heterocyclic ring structure having from 4 to 8 atoms in its ring structure, $R^{44}$ is absent and the carbon atom bearing the $R^{40}$ and $R^{41}$ substituents is covalently bonded to the carbon atom bearing the $R^{42}$ and $R^{43}$ substituents and $R^{40}$ and $R^{41}$ may each independently be fused with one of $R^{42}$ or $R^{43}$ to form a ring structure that includes the carbon atoms to which they are bound, $Y^1$ and $Y^2$ are each independently H, hydroxyl, halo, alkyl, alkynyl, amino, nitro, thio, imino, amido, phosphoryl, phosphonato, carbonyl, carboxyl, silyl, or an ether, thioether, sulfonyl, selenoether, ketone, aldehyde, ester or —(CH2)$_n$—$R^{23}$, $R^{23}$ is aryl, cycloalkyl, cycloalkenyl or heterocyclyl or polycyclyl, and n is zero or an integer of from 1 to 8, provided that the substituents of the complex of formula (4) are selected such that the complex is asymmetric, M is Co(III) or Cr(III), A is a counterion or nucleophile selected from carboxylate, hydroxide, alkoxide, thiolate, sulfonate, sulfonamide, isocyanate, isothiocyanate, and halide, and A' is a molecule methanol.

26. The catalyst of claim 22, wherein the chiral catalyst complex is in the form of free flowing crystalline solid particles having a particle size of from about 50 to about 100 micrometers.

27. The method of claim 18, wherein $R^{40}$ and $R^{42}$ are fused to, together with the carbon atoms to which they are attached, form a 1,2-cyclohexylene group.

28. The method of claim 18, wherein $R^{41}$, $R^{43}$, $Y^1$, $Y^2$, $X^2$, $X^4$, $X^6$ and $X^8$ are each H, and $X^1$, $X^3$, $X^5$ and $X^7$ are each t-butyl.

29. The method of claim 29, wherein $R^{40}$ and $R^{42}$ are fused to, together with the carbon atoms to which they are attached, form a 1,2-cyclohexylene group.

30. The method of claim 29, wherein $R^{41}$, $R^{43}$, $Y^1$, $Y^2$, $X^2$, $X^4$, $X^6$ and $X^8$ are each H, and $X^1$, $X^3$, $X^5$ and $X^7$ are each t-butyl.

* * * * *